(12) United States Patent
Ciarrocca

(10) Patent No.: US 7,232,439 B2
(45) Date of Patent: Jun. 19, 2007

(54) BIPOLAR TISSUE MORCELLATOR

(75) Inventor: Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 629 days.

(21) Appl. No.: 10/674,333

(22) Filed: Sep. 30, 2003

(65) Prior Publication Data
US 2005/0070892 A1  Mar. 31, 2005

(51) Int. Cl.
*A61B 18/18* (2006.01)
*A61B 17/32* (2006.01)
(52) U.S. Cl. ............................ 606/48; 606/46; 606/180
(58) Field of Classification Search .................. 606/41, 606/45, 48–50, 167, 170, 180
See application file for complete search history.

(56) References Cited

U.S. PATENT DOCUMENTS

| | | | | |
|---|---|---|---|---|
| 5,697,882 A | * | 12/1997 | Eggers et al. ............... | 604/114 |
| 5,810,806 A | * | 9/1998 | Ritchart et al. ............... | 606/45 |
| 5,899,915 A | * | 5/1999 | Saadat ......................... | 606/170 |
| 5,928,163 A | * | 7/1999 | Roberts et al. ............. | 600/567 |
| 5,957,884 A | * | 9/1999 | Hooven ........................ | 604/48 |
| 6,032,673 A | * | 3/2000 | Savage et al. .............. | 128/898 |
| 6,193,715 B1 | * | 2/2001 | Wrublewski et al. ......... | 606/45 |
| 6,565,561 B1 | * | 5/2003 | Goble et al. ................. | 606/41 |
| 6,659,105 B2 | * | 12/2003 | Burbank et al. ............. | 128/898 |
| 6,997,926 B2 | * | 2/2006 | Gellman et al. .............. | 606/46 |
| 2003/0055421 A1 | * | 3/2003 | West et al. .................... | 606/41 |

\* cited by examiner

*Primary Examiner*—Michael Peffley

(57) ABSTRACT

An endoscopic morcellator device and method for use is provided. The morcellator device includes an elongate shaft having a proximal end and a distal end and a lumen extending therethrough, a handle coupled to the proximal end of the shaft, at least one active electrode disposed about a periphery of the distal end of the shaft, at least one return electrode disposed at the distal end of the shaft and electrically insulated from the at least one active electrode, and at least one fluid conduit extending along the shaft and having an outlet at the distal end of the shaft.

11 Claims, 7 Drawing Sheets

BIPOLAR TISSUE MORCELLATOR

FIELD OF THE INVENTION

This invention relates generally to endoscopic tissue morcellators and specifically to a novel bipolar radio frequency (RF) morcellator that employs a conductive fluid media to enable highly efficient cutting of tissue with a plasma/vapor pocket.

BACKGROUND

Minimally invasive endoscopic surgeries and techniques are widespread in the medical world today due to the obvious benefits of reduced patient trauma and recovery times. These procedures typically involve making one or more incisions in the patient in proximity to the surgical target, and inserting a cannula or other surgical port through which the entire surgery is preformed by manipulating endoscopic instruments within the port. Many endoscopic surgical procedures require removing or excising body tissue or other matter (such as a tumor) having a size greater than the diameter of the cannula. To accomplish this, the tissue must be cut into small enough pieces, or otherwise reconfigured to enable it to be removed through the cannula. Tissue morcellators are a well known means by which to accomplish this result. U.S. Pat. Nos. 5,439,474, 5,443,472, 5,520,634, 5,562,694, 5,569,927, 5,879,358, 6,039,748, 6,193,715 and 6,468,228, all describe tissue morcellators of varying complexity that can be used to morcellate and/or extract tissue from an endoscopic surgery site. These instruments generally consist of a pistol-style handle 102 (see FIG. 1) with an elongate shaft 106 for endoscopic access. The distal tip of the shaft is equipped with a rotary cutting mechanism 100 for cutting tissue that comes into contact with it. The handle either possesses a motor or provides connection to an external motor for rotating the cutting mechanism at the end of the elongate shaft. The shaft of the instrument is completely hollow and equipped at the proximal end with an entryway to allow passage of a grasper or tenaculum 104 into the surgical site for the purpose of grasping (FIGS. 2a and 2b), pulling and guiding tissue into contact with the cutting element, and eventually removing the cut tissue out through the shaft (FIG. 2c). This entryway is generally equipped with one or more gaskets that seal to the shaft of the tenaculum when it is in use to preclude the loss of pneumoperitoneum.

Although functional, these devices are limited in that they are generally complex, expensive, and rely solely on sharp edges and other mechanical means (electric motors, mechanical screws) to cut tissue. Reliance on such mechanical means and sharp shearing surfaces is sub-optimal in that device performance will degrade as the edge dulls with use. In addition, sharp cutting edges present the risk of accidental tissue cutting or damage and provide no hemostatic capability. Another deficiency of these devices arises from the weight of the integral motors or drive cables required to couple the instrument to an external motor, which makes manipulation of the instrument both awkward and fatiguing.

Alternative mechanisms and devices for endoscopically cutting or dissecting tissue within the body have been developed. For example, U.S. Pat. Nos. 5,697,281, 5,697,536, 5,697,882, and 5,697,909, which are incorporated herein by reference in their entirety, describe bipolar electrosurgery technology that uses a plasma/vapor pocket to provide rapid tissue vaporization or cutting with reduced collateral tissue damage and improved hemostatic effect as compared to monopolar electrosurgery. These patents describe a custom generator which is capable of forming and maintaining this plasma bubble in a conductive fluid media, such as normal saline, and a collection of electrodes which can be used to cut and vaporize tissue. None of these devices, however, are morcellators, as none are designed to or capable of being used to excise and remove relatively large tissue volumes from the body.

Accordingly, there remains a need for an improved morcellator that provides rapid and efficient cutting and concomitant hemostasis without the need for sharp edges and mechanical drive mechanisms.

SUMMARY OF THE INVENTION

An endoscopic morcellator device is providing including an elongate shaft having a proximal end and a distal end and a lumen extending therethrough, a handle coupled to the proximal end of the shaft, at least one active electrode disposed about a periphery of the distal end of the shaft, at least one return electrode disposed at the distal end of the shaft and electrically insulated from the at least one active electrode, and at least one fluid conduit extending along the shaft and having an outlet at the distal end of the shaft. In one embodiment, the at least one return electrode is disposed about the periphery of the distal end of the shaft at a location proximal of the at least one active electrode. The device may also include a plurality of fluid conduits extending along the shaft and each having an opening at the distal end of the shaft, wherein the openings of the plurality of fluid conduits are disposed about the periphery of the distal end of the shaft.

In one embodiment, the periphery of the distal end of the shaft is substantially circular, and in yet another embodiment the device further includes an RF energy source electrically coupled to the at least one active electrode. The RF energy source may provide sufficient energy to create vapor pockets on a surface of the at least one active electrode, and the device may include a foot pedal for controlling energy delivered by the RF energy source. In another embodiment, the device further includes a fluid source in fluid communication with the at least one fluid conduit for providing fluid thereto.

In alternate embodiments, the at least one active electrode may be disposed distal of the at least one return electrode, or the device may have a plurality of active electrodes substantially equally spaced apart about the periphery of the distal end of the shaft. In yet another embodiment, the device includes a plurality of return electrodes positioned between successive ones of the plurality of active electrodes. In one embodiment, the at least one active electrode is electrically insulated from the at least one return electrode by an insulator disposed therebetween.

Also provided is a method for endoscopically morcellating a patient's tissue including the steps of providing an endoscopic morcellator having an elongate shaft having a proximal end and a distal end and a lumen extending therethrough, a handle coupled to the proximal end of the shaft, at least one active electrode disposed about a periphery of the distal end of the shaft, at least one return electrode disposed at the distal end of the shaft and electrically insulated from the at least one active electrode, and at least one fluid conduit extending along the shaft and having an outlet at the distal end of the shaft; advancing a tissue engaging device through the shaft; engaging at least a portion of a target tissue with the tissue engaging device; withdrawing the tissue engaging device and engaged tissue into the shaft lumen so as to cause the tissue to contact the at least one active electrode; supplying electrosurgical energy to the at least one active electrode thereby cut the tissue; and removing the tissue from the patient through the shaft lumen.

The provided device may also include a plurality of active electrodes substantially equally spaced apart about the periphery of the distal end of the shaft, and/or a plurality of fluid conduits extending along the shaft and each having an opening at the distal end of the shaft, wherein the openings of the plurality of fluid conduits are disposed about a periphery of the distal end of the shaft. In another embodiment of the provided device the at least one return electrode is disposed about the periphery of the distal end of the shaft at a location proximal of the at least one active electrode, and it may be that the periphery of the distal end of the shaft is substantially circular.

The device of the method may also include an RF energy source electrically coupled to the at least one active electrode, wherein the RF energy source provides sufficient energy to create a vapor pockets on a surface of the at least one active electrode. Finally, the device may further include a plurality of active electrodes and a plurality of return electrodes, wherein the return electrodes are positioned between successive ones of the plurality of active electrodes.

The present invention also provides a morcellator including an elongate shaft having a proximal end, a distal end and a lumen extending therethrough; at least one active electrode disposed about a periphery of the distal end the shaft; at least one return electrode at the distal end of the shaft and electrically insulated from the at least one active electrode; at least one fluid delivery conduit extending along the shaft, and having an opening at one end positioned in proximity to the at least one active electrode for delivering fluid in proximity thereto; a handle fixedly coupled to the proximal end of the shaft; a fluid delivery means in fluid communication with the at least one fluid delivery conduit for delivering fluid therethrough; and an RF energy source electrically coupled to the at least one active electrode.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Figure 1:
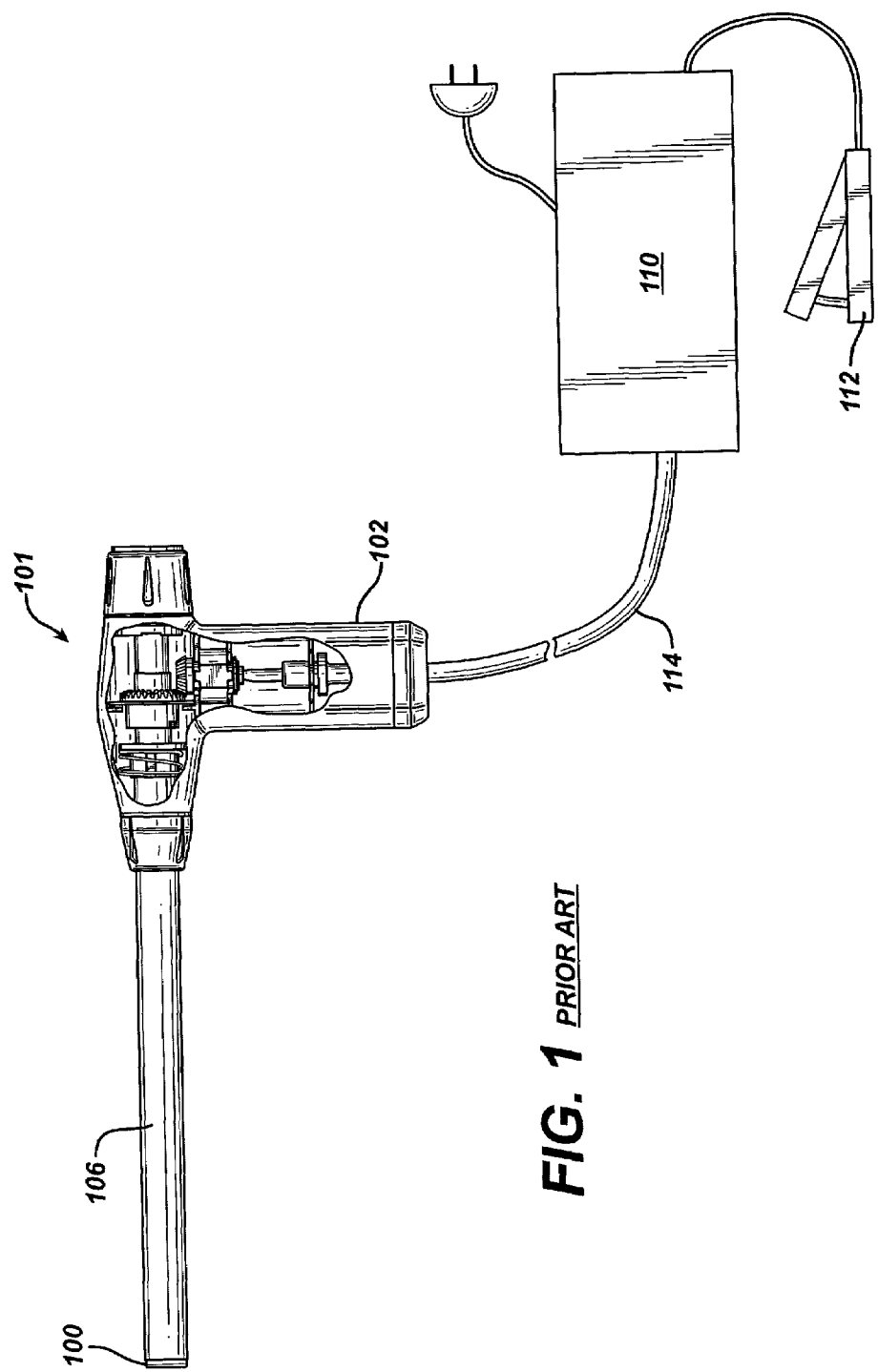
FIG. 1 illustrates an exemplary prior art motor-driven morcellator.

Referring now to FIG. 1, an exemplary prior art electromechanical morcellator 101 is shown connected to a motor drive unit 110 that is activated by way of a footpedal 112. The morcellator is coupled to the motor drive unit via a flexible mechanical drive cable 114. When the footpedal is activated, the motor drive unit rotates a central element of the mechanical drive cable. This rotating element of the mechanical drive cable works through a series of gears and other mechanisms within the morcellator instrument resulting in high-speed rotation of a tubular cutting element 100 which possesses a sharpened end.

Figure 2A:
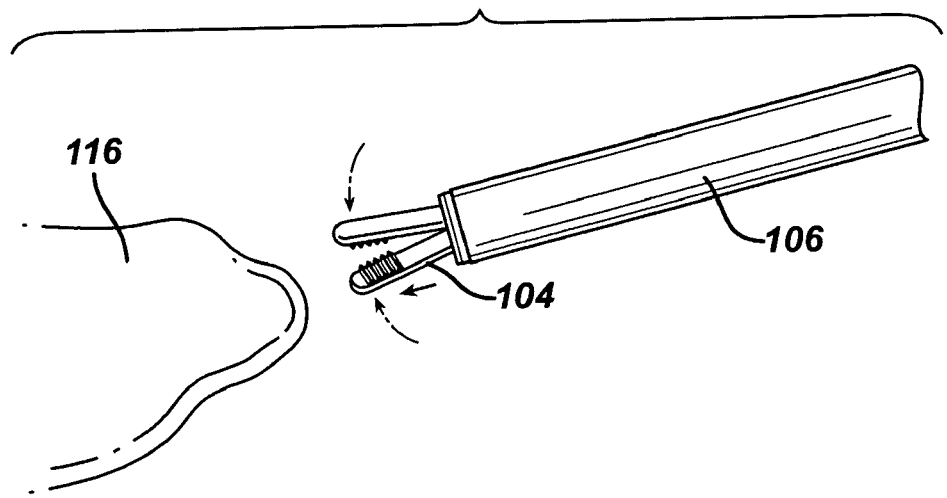
FIGS. 2a–c illustrate the operation of the exemplary prior art morcellator of FIG. 1.
Figure 2B:
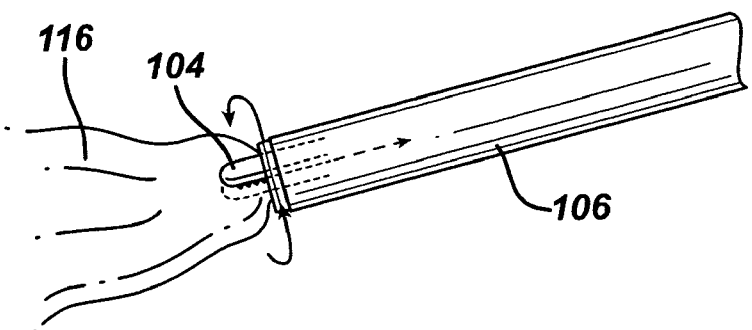
Figure 2C:
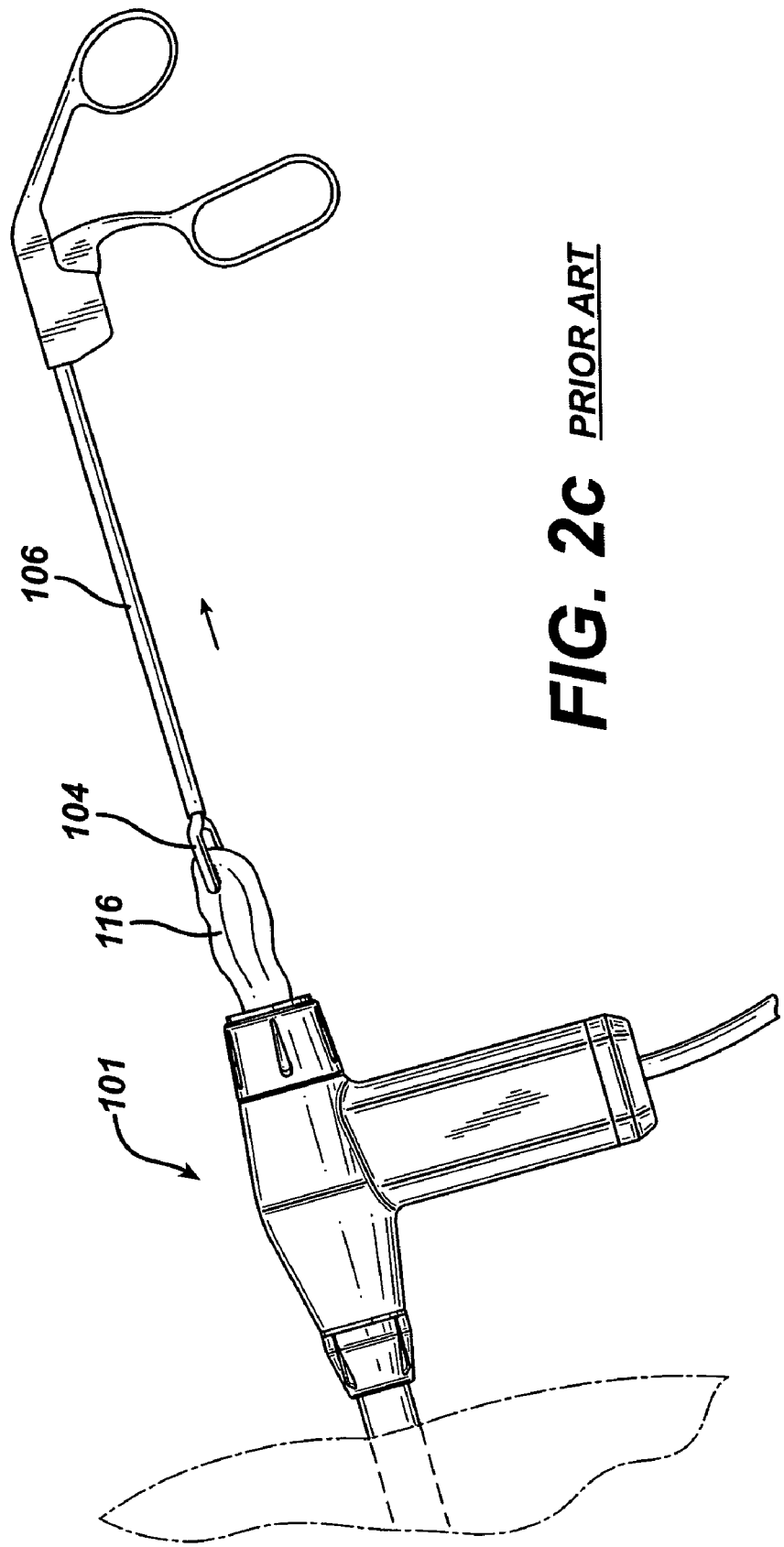

FIGS. 2a–c illustrate, in general, the operation of the prior-art electromechanical morcellator of FIG. 1. A grasper or tenaculum 104 is manually advanced through the a seal at the back of the handle and through the length of the hollow shaft 106 of the instrument and is used to grasp a section of target tissue 116. The tenaculum is subsequently withdrawn into the shaft, pulling the target tissue into contact with the cutting blade as shown in FIG. 2b. The morcellator is then activated, rotating the blade and shearing the tissue as it is pulled into the hollow shaft. FIG. 2c illustrates the tenaculum and the strip of excised tissue being withdrawn from the instrument.

Figure 3:
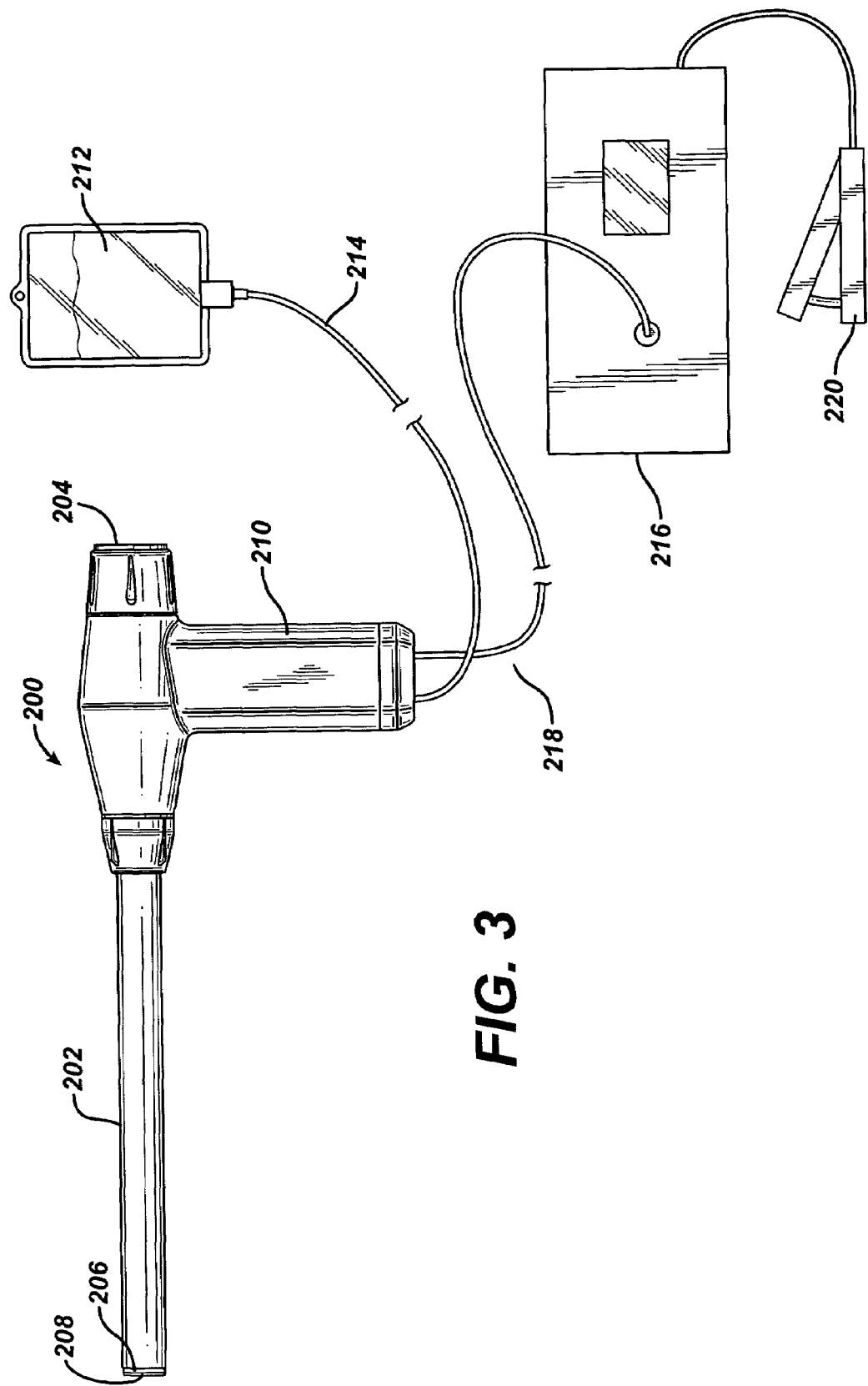
FIG. 3 is an elevational view of one embodiment of a morcellator according to the present invention connected to an electrosurgical generator and a fluid source.
Figure 4:
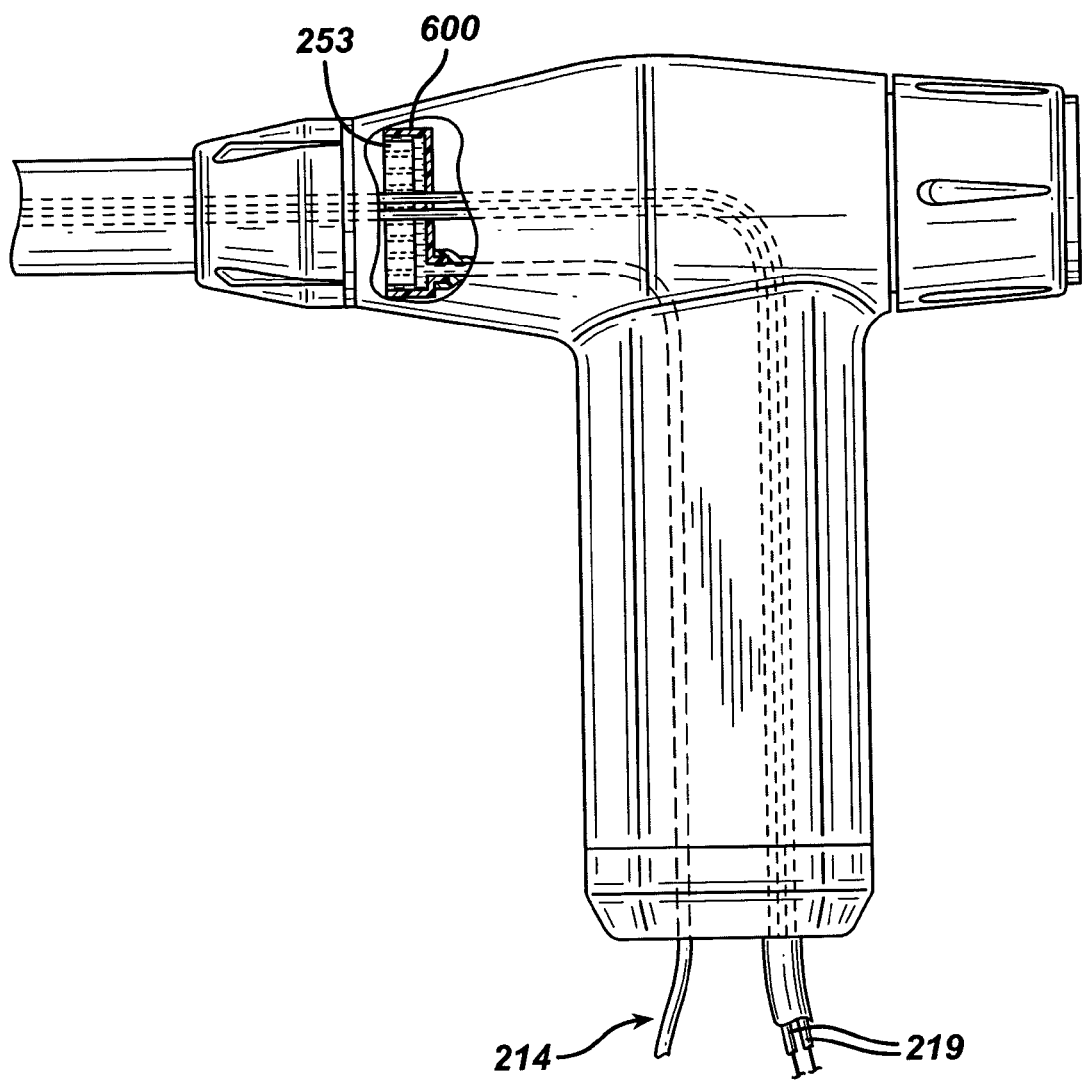
FIG. 4 is a side, cut-away view of the morcellator of FIG. 3.

Referring now to FIGS. 3–5, the present invention provides a novel morcellator device that improves and/or overcomes the disadvantages of known mechanical morcellators as described above. According to one embodiment shown in FIG. 3, the morcellator device 200 includes an elongate shaft 202 having a proximal end 204, a distal end 206, and a lumen 208 extending therethrough. Preferably, at least substantially the entire length of the shaft that could be extended through the cannula to the target site, except for the distal end, is surrounding by an insulating material. A handle 210 is coupled to the proximal end of the shaft, and is shaped and configured in any manner suitable to allow a user to manipulate the shaft, and particularly the distal end of the shaft, via the handle. The elongate shaft has a sufficient length such that the distal end of the shaft can be positioned within the body in the vicinity of the target tissue, while the handle remains outside the body. The lumen 208 is preferably circular in cross-section, and has a diameter sufficient to allow a tenaculum or other suitable tissue grasping device to be passed through in a manner similar to prior art morcellators.

The morcellator device 200 is coupled to a source of conductive fluid 212, such as normal saline or Ringer's Lactate, via an irrigation tube 214. This irrigation tube connects within the instrument to a manifold 600 (see FIG. 4) which is in communication with a collection of irrigation lumen 253 that run the length of the instrument shaft 202. This arrangement provides for a flow of conductive media to the electrode array at the distal tip of the instrument. The device is also coupled to a vapor-mode bipolar generator 216 by way of a two-conductor electrosurgery cable 218. This cable 218 is electrically connected by conductors to the electrode array at the distal tip of the instrument. The generator can be activated and controlled by a simple foot pedal 220. A suitable generator is manufactured by Artho-Care, Inc. of Sunnyvale, Calif.

Figure 5A:
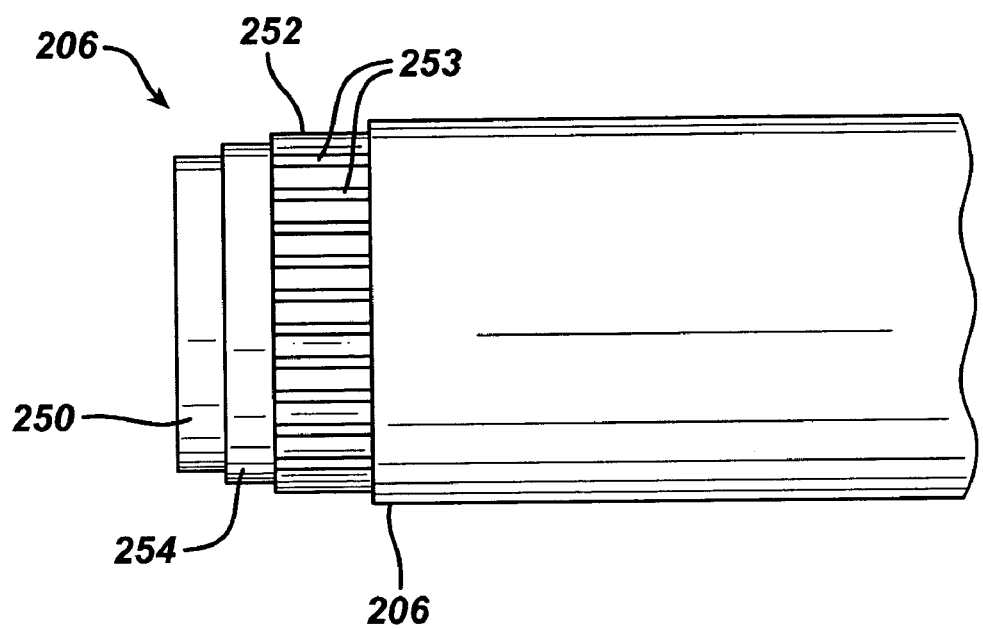
FIG. 5a is a side view of the distal end portion of the morcellator of FIG. 3.
Figure 5B:
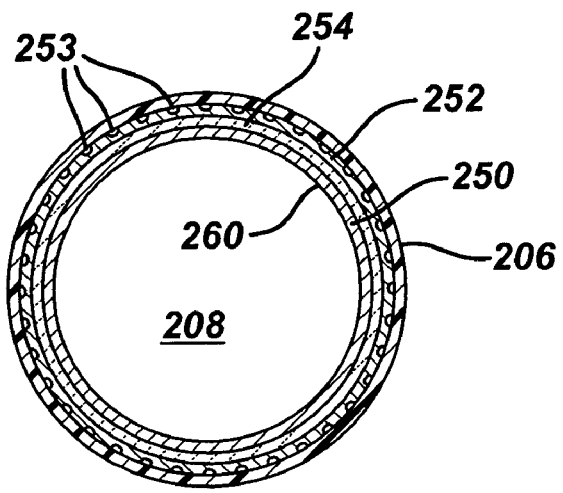
FIG. 5b is a front view of the distal end of the morcellator of FIG. 3.
Figure 5C:
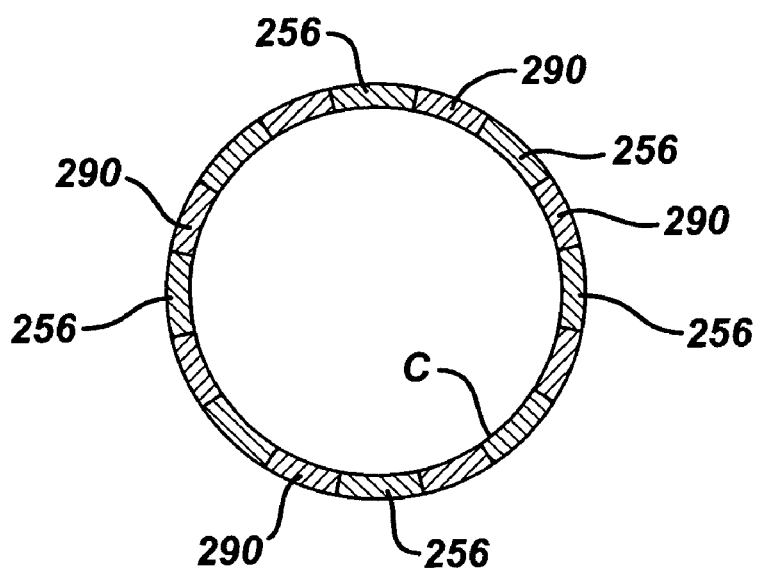
FIGS. 5c–d illustrate alternate electrode configurations for a morcellator according to the present invention.
Figure 5D:
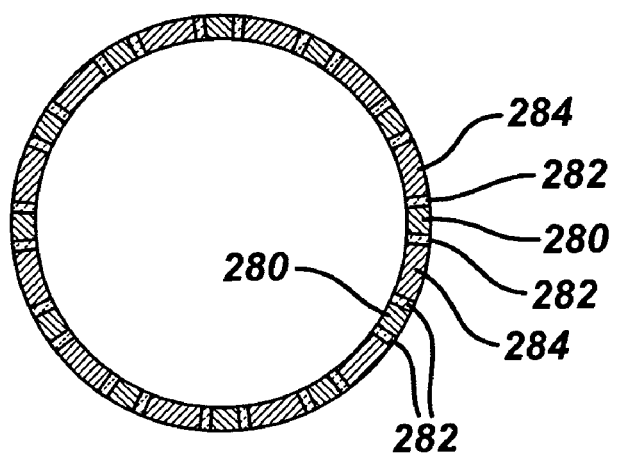

Referring now to FIGS. 5a–5d, positioned at the distal end 206 of the shaft is at least one active electrode 250 and at least one return electrode 252 electrically insulated from one another, preferably by an insulating material 254 disposed therebetween. The insulating material may be comprised of any suitable material, such as a ceramic, high-temperature thermoplastic, glass or silicone. In the embodiment illustrated in FIGS. 5a and 5b, a single active electrode is provided having a substantially circular cross-section and disposed about the periphery 260 of the distal end of the shaft. The return electrode 252 is also substantially circular in cross-section, and is similarly disposed about the periphery of the distal end of the shaft. In a preferred embodiment, the return electrode is positioned proximal of the active electrode, as shown in FIG. 5a. As is also illustrated in FIG. 5b, the return electrode may also be positioned concentrically around the active electrode. FIG. 5c illustrates an alternate embodiment having multiple independent active electrodes 256 spaced apart around the circumference C of the shaft at that location with insulation 290 in between. This embodiment may include a single return electrode also positioned around the circumference of the shaft at a location proximal of the active electrodes similar to that shown in FIGS. 5a and 5b. FIG. 5d illustrates yet another embodiment wherein multiple active electrodes 280 are similarly spaced apart around the circumference of the shaft, but wherein insulating material 282 and return electrodes 284 are positioned therebetween. Although specific electrode configurations have been described herein, those skilled in the art will readily understand that multiple other electrode configurations are also possible without departing from the scope of the present invention. The electrodes may be arranged in any configuration at the distal end of the shaft that will ensure sufficient cutting as the tissue is drawn into the morcellator by the tissue grasper.

The morcellator device described herein provides a simplified device for performing endoscopic morcellation. The device eliminates the need for complicated and cumbersome mechanical cutting components and the intricate mechanisms that drive them, yielding a lighter, more reliable, and more user friendly device. The presently disclosed device further reduces the risk of cutting or damaging surrounding tissue, and also provides hemostatic advantages.

It will be apparent from the foregoing, in which particular forms of the invention have been illustrated and described, that various modifications can be made without departing from the spirit and scope of the invention. Accordingly, it is not intended that the invention be limited, except as by the appended claims.

We claim:

1. An endoscopic morcellator device comprising:
a hollow elongate shaft having a proximal end and a distal end and a lumen extending therethrough, the lumen being sized and shaped for insertion of a tissue grasper therethough, and having a substantially uniform inner diameter;
a handle coupled to the proximal end of the shaft;
at least one active electrode disposed about a periphery of the distal end of the shaft;
at least one return electrode disposed at the distal end of the shaft having a substantially annular overall configuration concentrically disposed about the shaft and having an outer surface, the return electrode being electrically insulated from the at least one active electrode; and
a plurality of recesses formed in the outer surface of the at least one return electrode and extending along a length of the at least one return electrode to a distal end thereof, the plurality of recesses forming fluid conduits distinct and separate from the lumen,
wherein the elongate shaft contains no moving parts, and wherein activation of said at least one active electrode in the presence of fluid introduced through said fluid conduits cuts and/or vaporizes tissue in proximity thereto.

2. The device according to claim 1, wherein the at least one return electrode is disposed about the periphery of the distal end of the shaft at a location proximal of the at least one active electrode.

3. The device according to claim 1, wherein the periphery of the distal end of the shaft is substantially circular.

4. The device according to claim 1, further comprising an RF energy source electrically coupled to the at least one active electrode.

5. The device according to claim 4, wherein the RF energy source provides sufficient energy to create vapor pockets on a surface of the at least one active electrode.

6. The device according to claim 5, further comprising a foot pedal for controlling energy delivered by the RF energy source.

7. The device according to claim 1, further comprising a fluid source in fluid communication with the fluid conduits for providing fluid thereto.

8. The device according to claim 1, wherein the at least one active electrode is disposed distal of the at least one return electrode.

9. The device according to claim 1, further comprising a plurality of active electrodes substantially equally spaced apart about the periphery of the distal end of the shaft.

10. The device according to claim 1, wherein the at least one active electrode is electrically insulated from the at least one return electrode by an insulator disposed therebetween.

11. A morcellator comprising:
a) a hollow elongate shaft having a proximal end, a distal end and a lumen extending therethrough, the lumen being sized and shaped for insertion of a tissue grasper therethough, and having a substantially uniform inner diameter;
b) at least one active electrode disposed about a periphery of the distal end the shaft;
c) at least one return electrode at the distal end of the shaft having a substantially annular overall configuration concentrically disposed about the shaft and having an outer surface, the return electrode being electrically insulated from the at least one active electrode;
d) a plurality of recesses formed in the outer surface of the at least one return electrode and extending along a length of the at least one return electrode to a distal end thereof located in proximity to the at least one active electrode, the plurality of recesses forming fluid delivery conduits distinct and separate from the lumen;
e) a handle fixedly coupled to the proximal end of the shaft;
f) a fluid delivery means in fluid communication with the fluid delivery conduits for delivering fluid therethrough; and
g) an RF energy source electrically coupled to the at least one active electrode;
wherein the elongate shaft contains no moving parts.

* * * * *